United States Patent
Maggioni

[11] Patent Number: 5,395,346
[45] Date of Patent: Mar. 7, 1995

[54] DISPOSABLE SYRINGE WITH A RETRACTABLE NEEDLE

[76] Inventor: Tarcisio Maggioni, Via Colleoni, 5 - Palazzo Taurus A3, 20041 - Agrate Brianza (Milano), Italy

[21] Appl. No.: 210,137
[22] Filed: Mar. 17, 1994

[30] Foreign Application Priority Data

Jul. 26, 1993 [IT] Italy ............................ MI93A01669
Jan. 26, 1994 [IT] Italy ............................ MI94A0127

[51] Int. Cl.⁶ .................................................. A61M 5/00
[52] U.S. Cl. ...................................... 604/195; 604/110
[58] Field of Search ............... 604/110, 187, 192, 195, 604/243, 263

[56] References Cited

U.S. PATENT DOCUMENTS 4,950,241  8/1990  Ranford ........................... 604/110
5,047,016  7/1991  Dolgin et al. ................... 604/110
5,084,029  1/1992  Nacci et al. ..................... 604/195

Primary Examiner—John D. Yasko
Attorney, Agent, or Firm—Bucknam and Archer

[57] ABSTRACT

The present invention relates to a disposable syringe construction including a retractable or withdrawing needle, which comprises a cylindric body defining, at one end thereof, an end piece for the connection of the needle, and being open, at the other end thereof, for receiving a piston therein, provided with a sealing gasket.

The main feature of the invention is that the end piece is provided in its inside with a cutout for coupling with abutment legs of a hub element to which the point of the needle is connected, an outer collar being moreover provided, which can be applied to the end of the end piece so as to prevent the hub and related needle to be outwardly ejected.

6 Claims, 3 Drawing Sheets

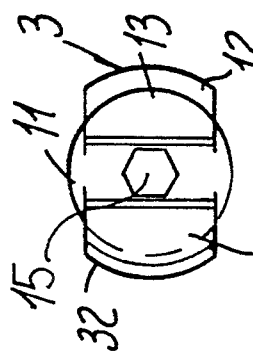
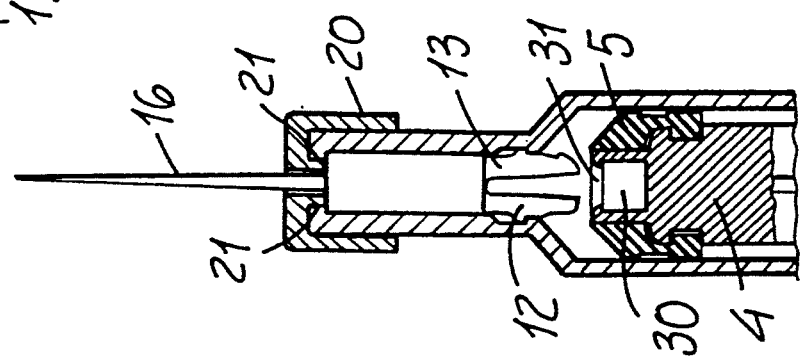
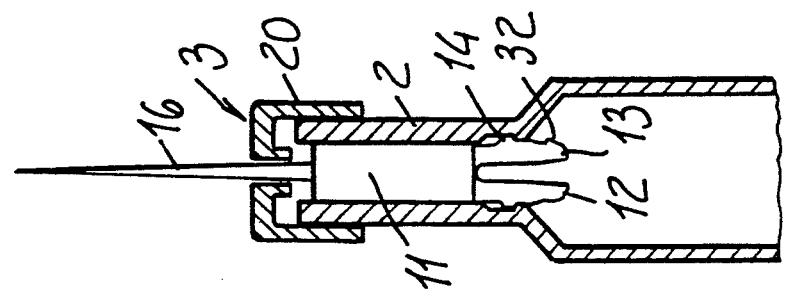
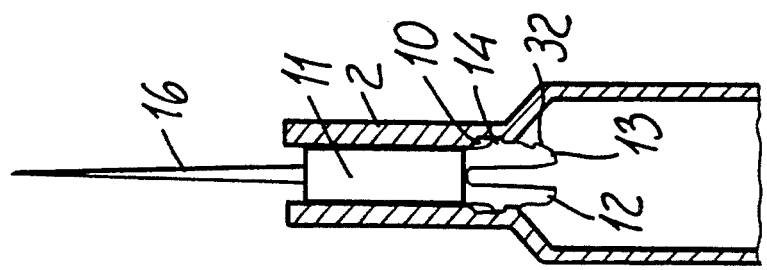
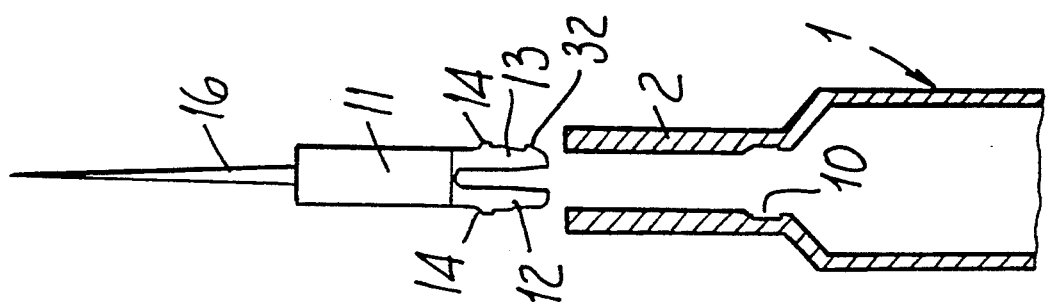

1

DISPOSABLE SYRINGE WITH A RETRACTABLE NEEDLE

BACKGROUND OF THE INVENTION

The present invention relates to a disposable syringe construction provided with a retractable or withdrawable needle.

As is known, a very important problem in making disposable syringes is that of providing a possibility of re-using said syringes and that of preventing the needle from accidentally injuring an user handling the needle syringe.

Prior solutions to solve the above mentioned problem usually provide to use syringes including resilient means for causing the syringe needle to be retracted inside the syringe.

These types of syringes, however, in addition to being very expensive, have the drawback that they involve a modification of the conventional use method of the syringes, since, as a puncture is performed thereby, it is anyhow usually necessary to overcome a resilient opposing force.

Other prior solutions, which do not provide to use resilient means, comprise connecting elements for coupling the needle to the syringe body, which connecting elements, however, do not provide a safe locking of the needle in its intended position and, moreover, being very complex from a construction standpoint.

SUMMARY OF THE INVENTION

Accordingly, the aim of the present invention is to overcome the above mentioned drawbacks, by providing a disposable syringe contruction, including a retractable needle, which affords the possibility of causing the needle to be easily withdrawn inside the syringe body, without the need of using return springs, while also providing the possibility of safely locking the needle in its intended use position.

Within the scope of the above mentioned aim, a main object of the present invention is to provide such a disposable syringe construction affording the possibility of causing the needle to be withdrawn inside the syringe by using very simple and mechanically reliable means.

Another object of the present invention is to provide such a disposable syringe construction which can be made by very simple component elements, thereby providing great economic advantages.

Yet another object of the present invention is to provide such a disposable syringe construction which, owing to its construction features, is very reliable and safe in operation.

According to one aspect of the present invention, the above mentioned aim and objects, as well as yet other objects, which will become more apparent hereinafter, are achieved by a disposable syringe construction, provided with a retractable needle, comprising a cylindric body defining, at an end portion thereof, an end-piece for connecting a needle and being open, at another end portion thereof, to receive a piston element provided with a plunger, characterized in that said end piece is provided with an inner cut-out for engaging with abutment legs of a hub to which said needle is connected, an outer collar being moreover provided, which can be applied to said end piece, by upsetting a portion of said end-piece, so as to prevent said hub and needle from being outwardly ejected.

BRIEF DESCRIPTION OF THE DRAWINGS

Further characteristics and advantages of the present invention will become more apparent hereinafter from the following detailed disclosure of a preferred, through not exclusive, embodiment of a disposable syringe construction, provided with a retractable needle, which is illustrated, by way of an indicative, but not limitative example, in the accompanying drawings, where:

FIG. 1 is a schematic cross-sectional exploded view showing the cylindric body of the syringe with the needle thereof connected to a hub or barrel element;

FIG. 2 is a schematic top plan view of the hub element;

FIG. 3 illustrates a connection step for connecting said hub element with the syringe needle in the end-piece of the cylindric body;

FIG. 4 illustrates the application of the collar to the syringe end-piece;

FIG. 5 is a cross-sectional view illustrating a method for affixing the collar element included in the syringe by upsetting the forming material thereof;

DESCRIPTION OF THE PREFERRED EMBODIMENT

Figure 6:
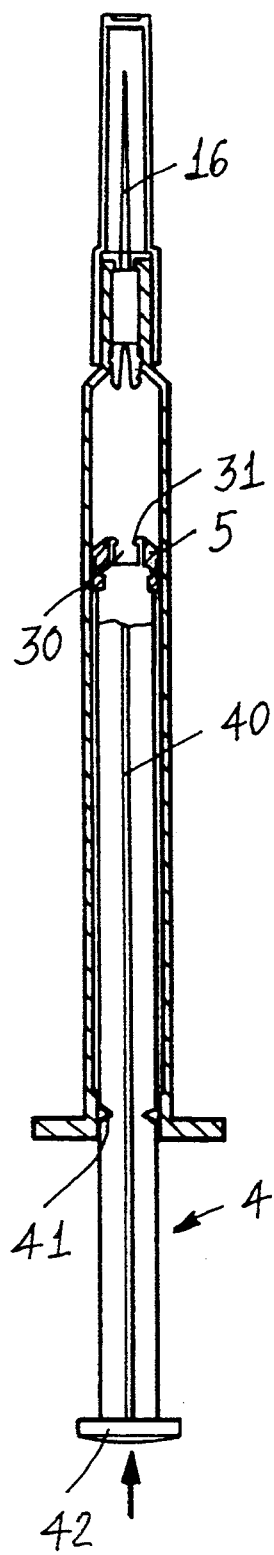
FIG. 6 is a cross-sectional view of the syringe in a ready of use condition.
Figure 7:
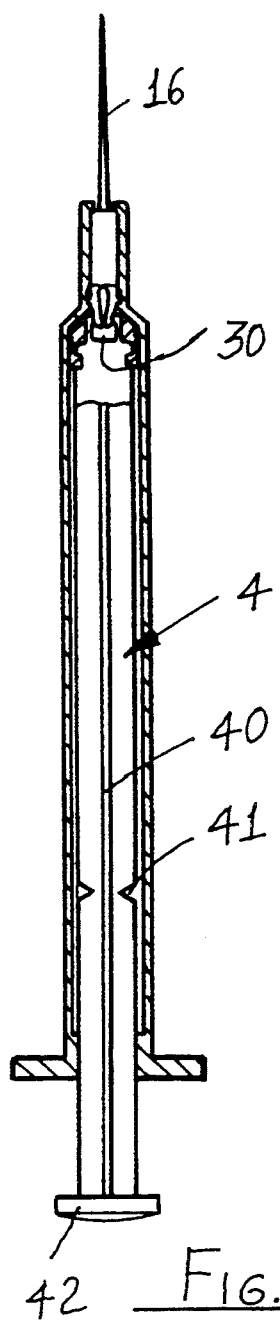
FIG. 7 represents the syringe at the end of a puncturing operation.
Figure 8:
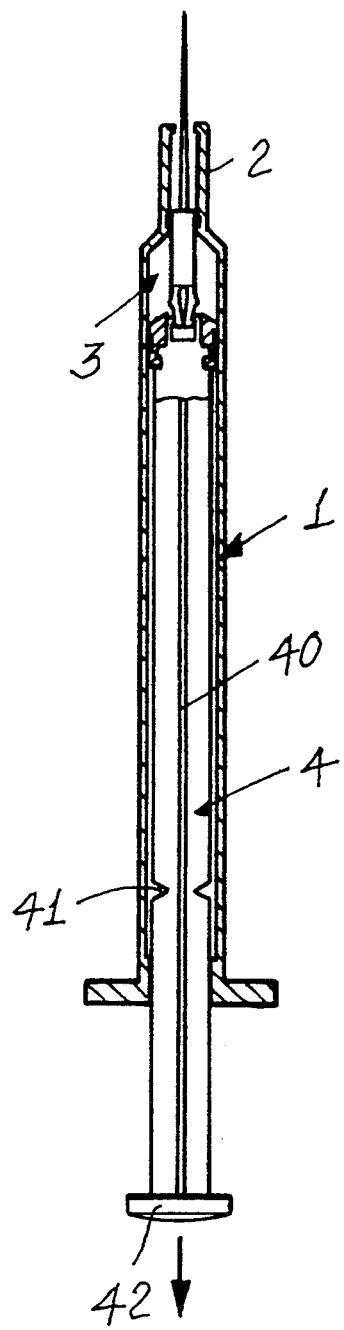
FIG. 8 illustrates an operating step in which the piston element to which the syringe needle is connected is withdrawn.
Figure 10:
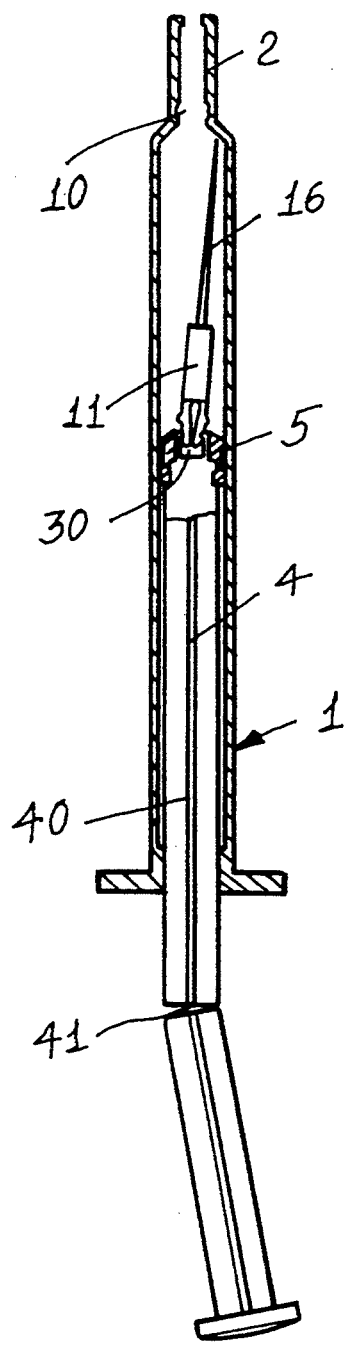
FIG. 10 is a cross-sectional view illustrating an operating step in which the piston is broken so as to prevent the syringe from being re-used.
Figure 9:
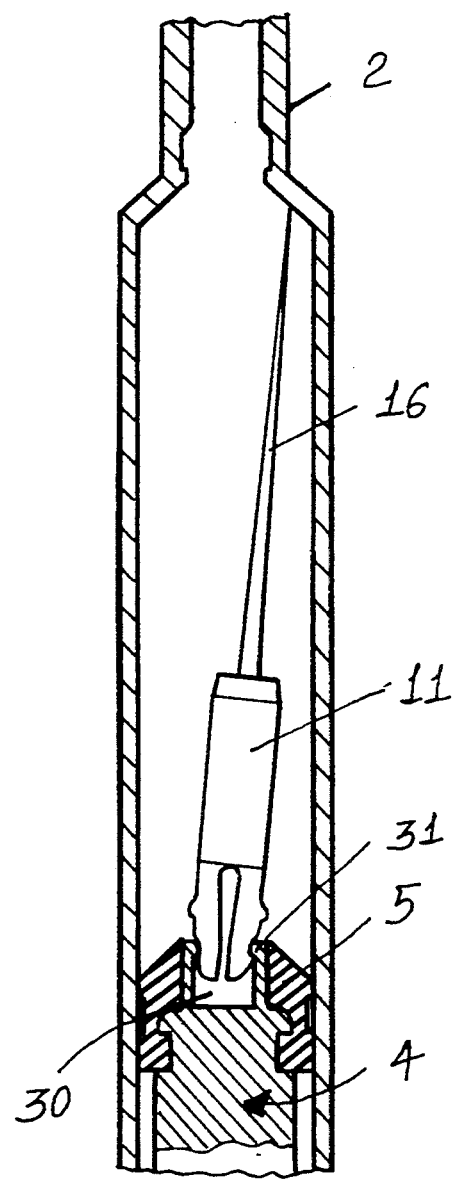
FIG. 9 is a cross-section view, on an enlarged scale, showing the syringe needle withdrawn inside the syringe cylindric body.

With reference to the number references of the above figures, the disposable syringe construction, provided with a retractable needle, according to the present invention, comprises a cylindric body 1 which is provided, at one end portion thereof, with an end-piece 2, to which a needle is connected, said needle being generally indicated at the reference number 3.

Inside the cylindric body 1, a piston can be engaged, generally indicated at the reference number 4, said piston being provided with a sealing gasket or rubber sealing element 5.

A first main feature of the present invention is that the end-piece 2 is provided, in its inside, with a cut-out portion 10 which operates as an engagement element for the drum portion or hub 11 of the needle 3.

More specifically, this drum or hub portion 11 is provided, at its inner end portion, with opposite lugs 12 and 13, which can be resiliently contracted, and including abutment legs 14 engaging in said cut-out 10 so as to prevent the needle from being withdrawn inside the cylindric body 1.

Moreover, the drum or hub 11 is provided with a polygonal hole 15, in which there is force engaged, in a per se known manner, the point 16 of the needle 3.

In order to provide a firm connection, after having introduced the needle 3 by urging the hub so as to cause the abutment legs 14 of the hub to be engaged in the cut-out 10, an outer collar 20 is applied, which, more specifically, is applied on the end portion of the end-piece 2 and being urged so as to upset the material, at the end of the end-piece, to provide a narrowing region, indicated at 21 in FIG. 5, adapted to operate as a locking element for preventing the needle 3 from being withdrawn from the cylindric body.

As shown, the piston 4 is provided, at the end portion of the plunger 5, with a blind hole 30, including a locking collar 31, adapted for engagement with the ends of the lugs 12 and 13 of the hub 11 of the needle 3, so as to cause them to be contracted, thereby causing said lugs to be connected inside the hole or seat 20, and a locking of the tooth element 32, provided on one of the lugs, for example the lug 13, with respect to the locking collar 31.

Thus, the needle is made rigid with the end portion of the piston.

By exerting a pulling force, and owing to the fact that the lugs 12 and 13 have been contracted, the legs 14 are disengaged from the cut-out 10, thereby the needle can be also disengaged and caused to be withdrawn inside the cylinder.

The provision of a single lug with a locking element, whereas the other lug operates as a guide element, causes the needle, as it is withdrawn inside the cylinder 11, to be tilted through few degrees, usually about 5°.

Thus, the needle point will be laterally displaced, thereby the needle can not be further withdrawn for a possible re-use of the syringe.

Moreover, as shown, the stem or rod 40 of the piston 4 is provided with notches 41, at an intermediate portion thereof, allowing the stem or rod to be easily broken, by removing the end portion including the pushbutton element 42, in order to provide a pushing force.

With the disclosed arrangement, there is provided a very functional syringe which can not be re-used, which is obtained by very simple means and which, anyhow, is specifically adapted to allow the needle to be always firmly held in its use position, whereas it is safely disengaged as the piston is withdrawn again.

The invention as disclosed is susceptible to several modifications and variations all of which will come within the scope of the inventive idea.

I claim:

1. A disposable syringe construction provided with a retractable needle held in a needle hub, comprising a cylindric body defining, at an end portion thereof, an end piece for firmly engaging said needle hub and being open at another end portion thereof, to receive a piston element provided with a plunger, wherein said end piece is provided with an inner cutout, said needle hub including resilient extending downwardly substantially opposite abutment legs provided with lugs engageable as said lugs are resiliently deflected toward one another in said inner cutout of said end piece, an outer collar being moreover provided which is engaged on said end piece to clamp said end piece therein to prevent said needle hub and needle from being outwardly ejected.

2. A syringe construction according to claim 1, wherein said lugs of said abutment legs provide a 90° type of connection with said inner cutout of said end piece.

3. A syringe construction according to claim 1, wherein said piston is provided, at an end portion thereof facing said needle with a blind hole closed by locking collar which is removably coupled with said lugs.

4. A syringe construction according to claim 1, wherein one of said lugs is provided with a locking tooth element which can be coupled with said locking collar the other of said lugs being adapted to operate as a guide element for coupling said lugs in said blind hole, by causing said abutment legs to be moved resiliently toward one another.

5. A syringe construction according to claim 4, wherein said locking tooth is so arranged as to cause said lug thereon said locking tooth is formed to be tilted, as said needle is withdrawn inside said cylindric body, to prevent said needle from being further withdrawn.

6. A syringe construction according to claim 1, wherein said piston is provided, at an intermediate portion of a piston rod thereof, with nothches adapted to allow an end portion of said piston to be broken in order to prevent said syringe from being re-used.

* * * * *